US012570999B2

(12) United States Patent
Büning et al.

(10) Patent No.: US 12,570,999 B2
(45) Date of Patent: *Mar. 10, 2026

(54) MUTATED ADENO-ASSOCIATED VIRAL CAPSID PROTEINS FOR CHEMICAL COUPLING OF LIGANDS, NANOPARTICLES OR DRUGS VIA THIOETHER BINDING AND PRODUCTION METHOD THEREOF

(71) Applicant: FRAUNHOFER-GESELLSCHAFT ZUR FÖRDERUNG DER ANGEWANDTEN FORSCHUNG E.V., Munich (DE)

(72) Inventors: Hildegard Büning, Hannover (DE); Anke Huber, Bad Peterstal (DE); Luca Perabo, Berlin (DE)

(73) Assignee: UNIVERSITÄT ZU KÖLN, Cologne (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/366,310

(22) Filed: Aug. 7, 2023

(65) Prior Publication Data

US 2024/0084326 A1    Mar. 14, 2024

Related U.S. Application Data

(62) Division of application No. 16/651,061, filed as application No. PCT/EP2018/076377 on Sep. 28, 2018, now Pat. No. 11,767,540.

(30) Foreign Application Priority Data

Sep. 28, 2017    (DE) .................................. 17193742.8

(51) Int. Cl.
*C12N 15/86* (2006.01)
*C12N 7/00* (2006.01)

(52) U.S. Cl.
CPC ............... *C12N 15/86* (2013.01); *C12N 7/00* (2013.01); *C12N 2750/14122* (2013.01); *C12N 2750/14143* (2013.01); *C12N 2750/14145* (2013.01)

(58) Field of Classification Search
None
See application file for complete search history.

(56) References Cited

U.S. PATENT DOCUMENTS 11,767,540 B2 * 9/2023 Büning .................. C12N 15/86
424/93.2
2004/0101824 A1    5/2004  Brauchle et al.
2006/0035378 A1    2/2006  Kochanek

FOREIGN PATENT DOCUMENTS

| WO | 2004/111248 A2 | 12/2004 |
| WO | 2007/089632 A2 | 9/2007 |
| WO | 2012/109570 A2 | 8/2012 |
| WO | 2014/124282 A2 | 12/2014 |
| WO | 2015/179321 A2 | 11/2015 |
| WO | 2019221992 A1 | 11/2019 |

OTHER PUBLICATIONS

Liu et al., "Site-Specific Modification of Adeno-Associated Viruses via a Genetically Engineered Aldehyde Tag", Small, 2013, 9, No. 3, 421-429.
Maersch et al., "Optimization of stealth adeno-associated virus vectors by randomization of immunogenic epitopes", Virology 397 (2010) 167-175.
Opie et al., "Identification of Amino Acid Residues in the Capsid Proteins of Adeno-Associated Virus Type 2 That Contribute to Heparan Sulfate Proteoglycan Binding", Journal of Virology, Jun. 2003, p. 6995-7006.
Yildiz et al., "Applications of viral nanoparticles in medicine", Current Opinion in Biotechnology 2011, 22:901-908.

* cited by examiner

*Primary Examiner* — Stacy B Chen
(74) *Attorney, Agent, or Firm* — WCF IP

(57)    ABSTRACT

In a first aspect, the present invention relates to a mutated adeno-associated virus (AAV) capsid protein or fragment thereof wherein a substitution of a wild type non-cysteine amino acid into a cysteine is present whereby the wild type non-cysteine amino acid is exposed on the outer surface of the capsid of an AAV particle. In a further aspect, a mutated AAV particle comprising the AAV capsid protein or fragment thereof according to the present invention is provided. In addition, a nucleic acid encoding the AAV capsid protein according to the present invention is identified together with a corresponding nucleic acid vector, in particular, a plasmid or a gene string. In addition, a host cell containing the nucleic acid vector or the nucleic acid according to the present invention as well as a composition comprising at least an infectious (transducing) AAV particle containing a mutated AAV capsid protein as defined herein together with a non-infectious AAV particle containing a mutated AAV capsid protein as e.g. defined herein is disclosed. Further, a method for the modification of a mutated AAV particle is disclosed allowing a specific modification of the same including an embodiment using a reagent addressing the cysteine residues for binding reaction such as a thioether binding.

25 Claims, 3 Drawing Sheets

Specification includes a Sequence Listing.

SEQUENCE LISTING

```
Sequence total quantity: 1
SEQ ID NO: 1              moltype = AA  length = 735
FEATURE                  Location/Qualifiers
source                   1..735
                         mol_type = protein
                         organism = Adeno-associated dependoparvovirus A
SEQUENCE: 1
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                  735
```

MUTATED ADENO-ASSOCIATED VIRAL CAPSID PROTEINS FOR CHEMICAL COUPLING OF LIGANDS, NANOPARTICLES OR DRUGS VIA THIOETHER BINDING AND PRODUCTION METHOD THEREOF

SEQUENCE LISTING

This application includes as the Sequence Listing the complete contents of the accompanying text file "Sequence.txt", created Aug. 7, 2023, containing 2775 bytes, hereby incorporated by reference.

In a first aspect, the present invention relates to a mutated adeno-associated virus (AAV) capsid protein or fragment thereof wherein a substitution of a wild type non-cysteine amino acid into a cysteine is present whereby the wild type non-cysteine amino acid is exposed on the outer surface of the capsid of an AAV particle. In a further aspect, a mutated AAV particle comprising the AAV capsid protein or fragment thereof according to the present invention is provided. In addition, a nucleic acid encoding the AAV capsid protein according to the present invention is identified together with a corresponding nucleic acid vector, in particular, a plasmid or a gene string. In addition, a host cell containing the nucleic acid vector or the nucleic acid according to the present invention as well as a composition comprising at least an infectious (transducing) AAV particle containing a mutated AAV capsid protein as defined herein together with a non-infectious AAV particle containing a mutated AAV capsid protein as e.g. defined herein is disclosed. Further, a method for the modification of a mutated AAV particle is disclosed allowing a specific modification of the same including an embodiment using a reagent addressing the cysteine residues for binding reaction such as a thioether binding.

BACKGROUND OF THE INVENTION

Adeno-associated virus (AAV), in particular, of serotype 2, has gained tremendous popularity as vector for gene therapy, but also as platform for vaccine development and as tool in pre-clinical research. That is, virus derived vectors represent one of the most popular gene delivery system for mammalian cells. The interest in particular with respect to AAV vector particles is based on several beneficial features including apathogenicity, high stability, ability to transduce both dividing and non-dividing cells, long term gene expression in post-mitotic or slowly proliferating cells and low immunogenicity. In addition, AAV vectors lack an intrinsic integrase activity and are therefore defined as non-integrating vector system. This is a main advantage compared to retro-/lentiviral vectors as it significantly reduces the risk of insertional mutagenesis. Further, AAV is apathogenic, which is an important aspect regarding vector safety. Further, high titer and highly purified AAV vector preparations are produced from tissue cultures followed sophisticated purification protocols enabled by the apathogenicity of the virus/vector and its stability.

The AAV virus is a member of the genus dependoparvovirus, which belongs to the parvoviridae (parvovirus family). AAV are composed of a single stranded DNA-genome of about 4.7 kB packaged in a non-enveloped icosahedral protein capsid. Until now at least twelve classical serotypes and over 100 variants of AAV have been isolated from human and non-human samples. These serotypes differ in epitopes recognized by antibodies against another serotype due to changes in the amino acid composition of their capsid proteins. A further consequence of these differences in amino acid composition is a difference in receptor usage and, thus, tropism. From all the serotypes known today, AAV serotype 2 (AAV-2) is the most characterized. AAV2 like the other serotypes contains a linear single stranded DNA genome encoding two genes named rep and cap. The cap gene encodes the three capsid proteins, VP1, VP2, VP3 and the assembly activating protein. VP1, VP2 and VP3 represent proteins obtained by alternative splicing and use of an alternative start codons. In the absence of VP1, non-infectious capsids are assembled. AAV serve as platform for the development of recombinant AAVs (=AAV vectors). In AAV vectors viral open reading frames are replaced by foreign nucleic acids such as a transgene expression cassette. AAV vectors deliver a single-stranded DNA encoding the sequence of interest flanked by the viral ITR structures. They are designed either in the natural genome conformation or as so called self-complementary vector genomes. Vector genomes are packaged during vector production into natural occurring capsids (serotype/variants) or engineered capsids.

A drawback of AAV vectors, in particular, AAV-2-based ones for in vivo applications is its broad tropism. Since AAV vectors are able to transduce a wide range of cell types, transduction efficacy of target organs is lowered, and administration of higher vector doses are required to achieve therapeutic target cell transduction levels. This raises safety concerns since immunogenicity and transduction of bystander tissues or organs could induce undesired side effects or adverse reactions. Furthermore, following systemic application in mice, non-human primates or humans, AAV vector particles tend to accumulate in the liver, which limits sufficient transduction of other target tissues. Hence, cell specific targeting has become a major focus in the development of AAV-based vectors for gene therapy. On the other hand, AAV vectors show a low transduction efficiency for certain clinically relevant cell types such as endothelial cells due to cell type specific barriers towards AAV transduction.

However, the AAV vector particle is considered to be an appropriate measure for gene therapy since they transduce in vivo and ex vivo non-dividing and proliferating cells. Significant improvements of AAV vectors with respect to their specificity occurred mainly by direct or indirect modification of the capsid, which represents the interface to the cellular receptors, intracellular structures and antibodies. The viral capsid consists of three capsid proteins VP1, VP2 and VP3 assembled together in an approximately 1:1:10 ratio and arranged in an icosahedric structure (e.g. Büning H et al J. Gene Met., 2008, 10, 717-713).

Different approaches have been conducted to change the tropism of a given AAV vector, e.g. exploitation of alternative serotypes for example by pseudotyping. However, redirection of the tropism and/or an increase of the specificity is difficult to obtain with that method. Therefore, alternative strategies have been developed such as genetic modification of the capsid proteins in order to tailor the host-AAV interaction and regulate the so-called cell entry.

For example, EP 2 158 211 B1 identifies structure protein insertions having a length of 4 to 13 amino acids being an epitope, thus, allowing cell targeting accordingly. In addition, approaches have been conducted for substituting specific amino acids present in the capsid proteins.

Further US 2009/0202490 A1 identifies a recombinant AAV vector comprising mutant capsid proteins, wherein the recombination was based on at least one amino acid substitution relative to the corresponding parental AAV capsid protein. The mutations described therein allows to alter properties of the AAV vector particles, like increased or decreased heparin binding affinity relative to the wild type AAV and/or altered infectivity of particle or cell types.

Finally, another strategy consists in attaching to the outer surface of the vector particle foreign molecules that can mediate specific interaction with cellular receptors expressed on the membrane of targeted cell types.

Chemical modifications of amino acids present on the surface or on the exterior of the capsid surface have been discussed. These modifications include binding of biotin for allowing coupling of further components via e.g. streptavidin. Recently, Kreppel et al, Molecular Therapy, 2005, 12, 1, 107-117 used a combination of a genetic and chemical targeting approach for adenovirus whereby in a first step genetically a cysteine containing motive was introduced into the solvent-exposed fiber HI loop of adenovirus followed by coupling of transferrin as a targeting ligand via the introduced cysteine residues. Coupling was achieved by formation of thioether or disulfide bonds. Whilst the first is covalent, the later can be separated after cell entry in the endosome, which might be necessary in some applications. The translation of this strategy to the AAV capsid resulted in low titers as cysteine residues are not tolerated when introduced by rational design.

WO 2012/149160 A2 identifies viruses modified with unnatural moieties and methods of use thereof. Therein, the strategy for modification of the capsid proteins is based on introducing the unnatural amino acid moieties, which eventually allows to introduce further groups.

That is, non-covalent and non-genetic binding strategies have been designed for modifying the capsid of AAV vector particles as well as increasing specificity overcoming the problems in connection with the broad tropism of the vectors. Alternatively, genetic modification may occur by typically insertion of fragments allowing targeting or modification accordingly.

However, the current methods for genetic modification rely on protein-based ligands in particular small peptides that on one hand show a low specificity and affinity and on the other hand do not allow to use recent developments such as single chain antibodies, aptamers etc. DARPin have been introduced as alternative to antibodies for genetic modification of AAV capsids, but need to be fused to VP2, a non-essential capsid protein. Thus, also DARPins have shown high target selectivity when genetically fused to wild type receptor blinded AAV particles, production of respective targeting vectors is extremely laborious, time-consuming and results in low titers.

SUMMARY OF THE INVENTION

By the here described invention a novel platform for the modification, like covalent modification, of AAV capsid has been developed allowing to

- use peptides and whole proteins as covalently attached ligands-if desired permanently attached-without the need for genetic fusion to one of the capsid proteins;
- use of single chain antibodies or other proteins that need to be modified intracellularly to gain function;
- use of the whole spectrum of non-proteinous ligands including aptamers;
- use of nanoparticles as binding partners;
- to couple a further or multiple AAV particles e.g. to enlarge the coding capacity;
- to couple antigens or immune modulatory molecules to enhance AAV's application in vaccine approaches;

- to couple drugs employing the AAV vectors system (natural serotypes or targeting vectors) for drug delivery;

The underlying problem of the invention is solved by the subject matter according to the claims.

The inventors developed a mutated adeno-associated virus (AAV) capsid protein representing a general platform for further modification, namely, chemical modification for covalent binding of additional molecules.

That is, in a first aspect, the present invention relates to a mutated AAV capsid protein or fragment thereof wherein an amino acid of the wild type adeno-associated virus capsid protein of SEQ ID No. 1 or fragment thereof or homolog of SEQ ID No. 1 have a substitution of a wild type non-cysteine amino acid into a cysteine, in particular, where the wild type non-cysteine amino acid is present on the outer surface of the capsid when the capsid is present as AAV particle allowing chemical modification.

This capsid protein or the fragment thereof are proteins or fragments allowing the formation of an AAV particle.

In a further aspect, a mutated AAV particle comprising the AAV capsid protein or fragment thereof according to the present invention is provided.

In addition, the present invention relates to a nucleic acid encoding the AAV virus capsid protein or fragment thereof according to the present invention. In addition, a nucleic acid vector, in particular, a plasmid comprising the nucleic acid molecules according to the present invention is disclosed as well as host cells containing said nucleic acid vector or said nucleic acid according to the present invention.

Moreover, a composition comprising an infectious AAV particle having the mutated AAV capsid protein according to the present invention and a non-infectious AAV particle containing a mutated AAV capsid protein having substitutions of at least one of R585A and R588A, whereby the infectious AAV particle is linked to at least one non-infectious AAV particle is provided. Further, a method for the modification of mutated AAV particle according to the present invention based on binding of the AAV particles to solid substrates including column purification techniques is mentioned. Finally, the use of the composition according to the present invention for transfection of target cells is disclosed.

DETAILED DESCRIPTION OF THE PRESENT INVENTION

Figure 1:
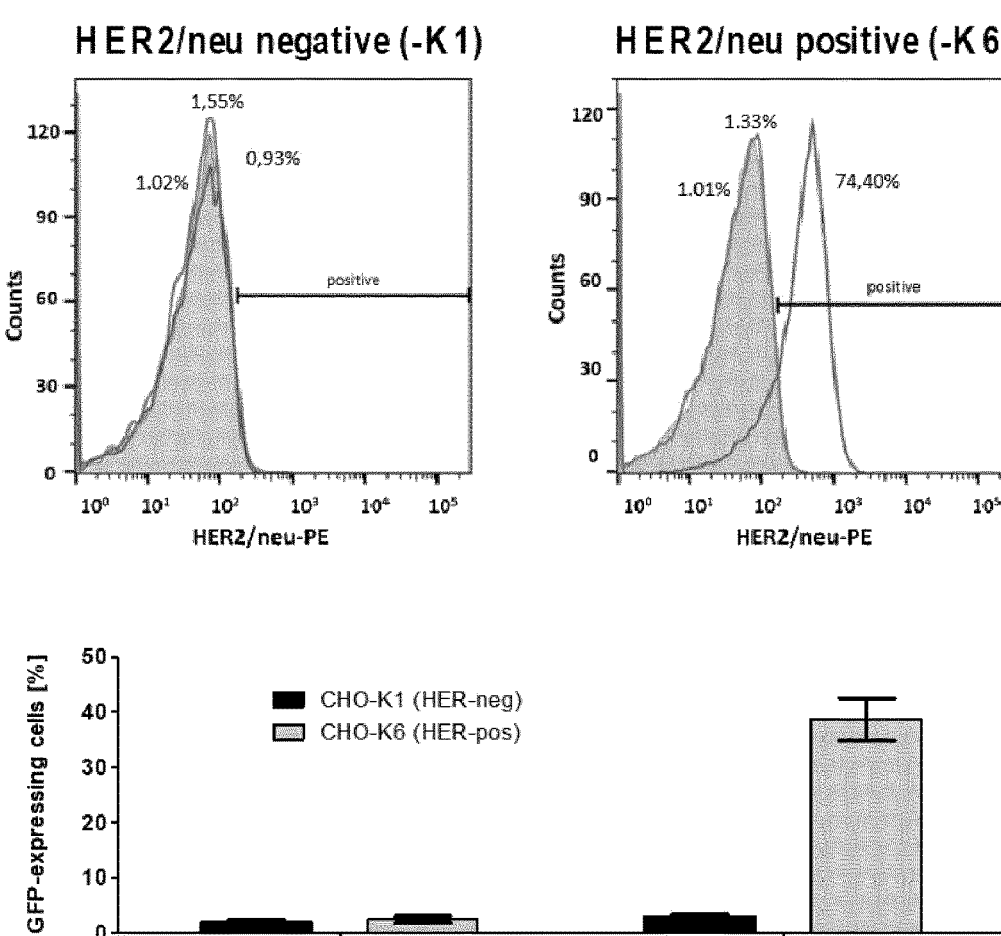
FIG. 1. Receptor targeting through genetic-chemical targeting. $C7^{\Delta HSPG}$ vector preparations were coupled with DARPins specific for Her2/neu, a surface molecule overexpressed on many tumor cells, via a bispecific linker. The latter contained a maleimide moiety to form a stable thioether bond with the cysteine residues on the capsid and a Dibenzocyclocysteine part to react with an azido-group at the DARPin. Chinese Hamster Ovarian (CHO) cell lines either negative for Her2/neu (CHO-K1, left FACS blot) or stably modified to express Her2/neu (CHO-K6, right FACS blot) were then incubated with $C7^{\Delta HSPG}$ vector preparations covalently coupled (AAV-$C7^{\Delta HSPG}$-DARPin) or not (AAV-$C7^{\Delta HSPG}$) with DARPin 9.29. All vectors encoded for enhanced green fluorescent protein (GFP). Percentage of transgene expressing cells was determined by FACS 48 hrs post transduction

The inventors developed a mutant AAV capsid protein or a fragment thereof allowing simple chemical modification for linkage of desired labeling groups, drugs, immune modu-latory molecules, antigens or targeting molecules as well as other virus particles.

The vector particles as well as the capsid proteins are characterized in having newly introduced cysteine residues by mutation at predetermined sites on the exterior of the capsid of AAV particle enabling chemical modification taking advantage of the thiol group present in the cysteine residue.

As used herein, the term "fragment thereof" refers to a protein or a polypeptide derived from the mutated cysteine protein of Seq ID No. 1 having the respective cysteine substitution. Typically, the size of the fragment is at least 50%, like at least 70%, 80%, 90%, like 95% of the size or length of the sequence it refers to.

The term "mutated AAV capsid protein" means a capsid protein that has at least one mutation of a non-cysteine amino acid to a cysteine residue compound to the respective capsid protein of the wild type virus, in particular, where the wild type non-cysteine amino acid is present on the outer surface of the capsid when the capsid is assembled as an AAV particle.

The term "homolog of SEQ ID No. 1" refers to the capsid protein sequence of the other AAV serotypes. That is, the homologs are serotype capsid proteins derived from the other AAV serotypes. An overview is given in Vance M. A., et al, DOI: 10.5772/61988.

The term "outer surface of the capsid" identifies the exterior of the capsid, which is accessible to chemical modification. The term "outer surface of the capsid" is used interchangeably with the term "exterior of the capsid".

The term "linker group" refers to a group allowing linkage by covalent or non-covalent bonds.

The term "targeting molecule" refers to a molecule allow-ing targeting of AAV particle as described herein to target cells.

The terms "particle", "vector particle", or "vector" iden-tify a capsid either without DNA or with containing the DNA. The term "AAV" refers to the adeno-associated virus itself or the derivatives thereof including recombinant AAV vector particles wherein the term "AAV wild type particle" designates the adeno-associated virus acid occurs in nature. The term "AAV" or the respective recombinant AAV vector particle and AAV wild type particle includes the at least twelve different serotypes known in the art. The AAV of human serotype 2 is also mentioned as AAV-2 or AAV-2 particle. The recombinant AAV or recombinant vector par-ticle is an AAV wherein the genome of the virus is substi-tuted with a vector genome, namely a foreign DNA to be introduced into the cell.

The term "target cells" or "target tissue" as used herein refers to specific cell types or tissues representing the target as defined by the targeting molecule covalently linked to the mutated AAV capsid proteins or fragments thereof according to the present invention.

The term "nanoparticles" as used herein refers to inor-ganic nanoparticles as known in the art as well as to other AAV particle. Further nanoparticles include other vesicles of nanometer size including exosomes, liposomes, micelles, colloidal particle, composite particle, organic particle, nano-structured vesicles or other types of nanometer-sized non-viral vectors.

The term "covalent" as used herein revers to a covalent linkage which may be in form of a permanent linkage or in form of a transient linkage, e.g. in case of disulfide bridges.

The present inventors recognized that introducing cyste-ine amino acid residues into the capsid protein or fragments thereof allowing the formation of the virus/vector capsid, namely, the formation of AAV particles, allow for modifi-cation of the viral capsids. In particular, the cysteine residues can be modified via the thiol group present therein. Hence, enabling new strategies for targeting and, in particular, cell entry targeting as well as for optimizing known strategies e.g. trans-splicing strategies as well as vaccine strategies.

In an embodiment of the present invention, the substitu-tion of the non-cysteine amino acid in cysteine residues is at least one substitution at position 446, 458, 459, 525, or 551 of the sequence shown in SEQ ID No. 1, or the homologeous residues of cap gene of one of the other serotypes as described in art. These cysteine residues are present on the exterior of the capsid and particles, thus, are accessible for chemical modification.

The sequence of SEQ ID No. 1 correspond to the amino acid sequence encoded by the cap gene. That is, the substi-tution is a substitution of S458C, R459C, or N551C.

In a further embodiment of the present invention, the mutated AAV capsid protein or fragment thereof is a protein or fragment thereof when at least at position N458 and N551 of SEQ ID No. 1 to a cysteine is present.

Moreover, the capsid protein may comprise either a substitution of R459M or a substitution of R459C. Further, a substitution of A493D and/or N449I may be present. In an embodiment, the mutated AAV capsid protein or fragment thereof is a protein or fragment thereof having the following substitutions: N449I, S458C, R459M, A493D, N551C.

It has been recognized that the cysteine substitutions allow to modify the capsid protein present in the vector or particle easily without deteriorating the activity thereof.

The particle remains infectious although substitution and, in addition, modification of at least one of the cysteines is present.

In a further embodiment, the particle or vector is a non-infectious particle. For example, the non-infectious particle is a particle having a mutated AAV capsid protein or fragment thereof having a mutation of at least one of the substitution at position R585A or R588A.

It is known that the mutation of the capsid protein at positions 585 and 588 result in a significant reduction of infectivity. This exchange allows to ablate the tropism of AAV. Namely, these two arginine residues 585 and 588 have been described as key residues of the HSPG (heparan sulfate proteoglycan) binding motive.

The skilled person is well aware of other suitable modifications of the AAV capsid protein or a fragment thereof rendering a vector particle containing the same are non-infectious.

In an embodiment of the present invention, the mutated AAV capsid protein or fragment thereof is a mutated AAV capsid protein or fragment thereof derived from AAV-2. As mentioned, the mutation introducing cysteine which are present on the exterior or outer surface of the capsid where the capsid protein is present in an AAV particle or is part of an AAV particle allows to chemically modify said capsid or particle. The thiol group present in the cysteine residue enables various covalent or non-covalent binding of molecules by forming disulfide bonds or thioether bonds.

Thus, the present invention relates in another aspect to a mutated AAV capsid protein or fragment thereof whereby the cysteine further links to a labeling group, such as a fluorescence labeling group, or a group for labelling capable of allowing click chemistry with an acid, thus, allowing linkage of other molecules by the wellknown click chemistry mechanism. Moreover, the cysteine allows to link a targeting molecule, e.g. linking the targeting molecule further by click chemistry with azide. The azide chemistry include linkage of a ligand by a maleimide binding whereby the linkage to the cysteine is via thioether group formation. The term "link", "links" or "linking" refers to covalent binding of the respective group to the capsid protein via the cysteine residue.

Figure 6:
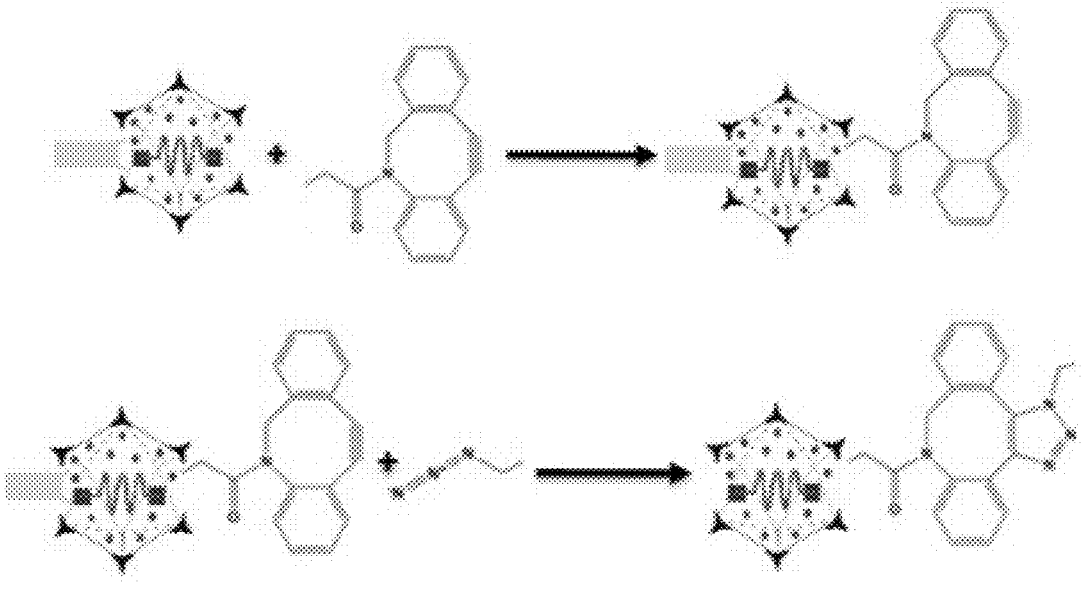
FIG. 6: an illustration of a click chemistry mechanism.

For example, in case of click chemistry, FIG. 6 shows a mechanism that may be possible.

Alternatively, the covalent binding of ligands comprising a nucleic acid residue, like protein ligands, may be carried out by maleimide based linkage.

That is, all kind of ligands or groups may be covalently attached to the mutated capsid protein or homolog or fragment thereof according to the present invention by the thiol group present at the substituted cysteine residues.

Said ligands or groups include labeling groups. Labeling groups may be based on chromophores, like fluorescence labeling groups or other types of linkage groups like biotin enabling the labeling, and thus, detection, of labeled compounds. In this aspect, the label is a marker allowing detection of the labeled capsid protein or AAV particle containing in the same.

In a further aspect, the ligand or group may be other types of peptide or nonpeptide-based ligands. These ligands may be ligands enabling binding to specific predetermined target cells, namely targeting molecules or targeting groups. For example, the targeting molecule for targeting the mutated protein or the AAV particle containing the same to the predetermined target, like a cell, is a ligand of a receptor expressed specifically by said target cell. The skilled person is well aware of suitable targeting molecules and targets present on these cells accordingly.

That is, a non-infectious vector particle as described herein may be targeted to a targeting cell by suitable targeting molecules bound covalently on the surface of said non-infectious vector particle. Thus, the non-infectious vector particle is rendered infectious by covalently binding the targeting molecule (ligand) on the surface of said vector.

In addition, the presence of the cysteine linkage groups allowing a click chemistry with azide based components. The skilled person is well aware of the reagents suitable for click chemistry.

Generally, the group which may be attached covalently via thioether bond or via disulfide bond is a molecule of interest which may be a probe, a therapeutic molecule, antibody, cytotoxin, immune modulatory molecule, but also non-infectious virus/vector particles.

As noted, the probe may be a label like a fluorescent or a chemoluminescent compound and/or an enzyme or a biotin.

The term "cytotoxin" as used herein, refers to a compound being cytotoxic on a target. For example, the cytotoxin comprises an anti-cancer toxin. In this connection, cytotoxic molecule refers to any molecule that reduces proliferation and/or viability of a target cell, preferably, not necessarily, killing the target cell. In a preferred embodiment, the cytotoxic molecule is an anti-cancer toxin.

The skilled person is well aware of suitable cytotoxic agents described in the art either in form of small drug molecules or in form of nucleic acid molecules or amino acid-based molecules.

Further, the term "therapeutic molecule" refer to a molecule that reduces, delays and/or eliminates undesirable pathologic effects in a cell, tissue, organ and/or animal. The therapeutic molecule may have cytotoxic activity, thus, there is an overlap of the possible molecules bound to the mutated AAV capsid protein or fragment thereof according to the present invention. For example, the therapeutic molecule is a nucleotide sequence encoding a suicide gene or silencer nucleic acid sequence.

In addition, the ligand may be an antibody or antigen binding fragment, the skilled person is well aware of suitable embodiments of antibodies including single chain antibodies and antibody fragments. The term "antibody" includes also the embodiment of affinity bodies or affibodies as described in the art. Moreover, the ligand may be an aptamer.

In addition, the ligands may be antigens or epitopes or immune modulatory molecules.

Moreover, the ligand may be a non-infectious virus particle as mentioned before. The non-infectious virus particle may be an AAV particle or a non-AAV virus particle.

That is, a co-delivery of vector particles composed of a vector particle having the mutated AAV capsid protein or fragment thereof according to the present invention in combination with a further vector particle, in particular, a non-infectious vector particle which is covalently linked with the mutated vector particle is provided. Thus, it is possible to allow trans-splicing technology, i.e. connection of two or more vector genomes through a cellular splice event enlarging thereby the coding capacity of AAV vectors. The infectious particle coupled to a non-infectious particle, e.g. so-called receptor blinded particles as a complex, will guide the complex towards the cell and mediate cell infection of the whole complex including the non-infectious particles. Thus, this technique allows to overcome the limited capacity of AAV vectors enabling the transduction of cells with a dual vector system, thereby increasing the capacity of components introduced into the cells. Thus, it is possible to enable trans-splicing or two component systems in vivo. Further, a dual vector system wherein both vectors are non-infectious vectors and further wherein one of said vectors have a targeting ligand allowing specific targeting is provided. This systems allows a targeting independent of the tropism of the AAV particle.

Hence, in a further aspect of the present invention, a mutated adeno-associated virus (AAV) particle also named vector particle comprising the adeno-associated particle virus capsid protein or a fragment thereof according to the present invention is provided. This particle is a particle allowing further chemical modification at the mutated adeno-associated particle virus capsid protein or fragment thereof according to the present invention.

In an embodiment, the particle according to the present invention comprise further a linker or linking group, like a targeting molecule, allowing coupling of at least a second, different mutant adeno-associated virus particle. Using this at least dual vector system allows to mediate cell entry of otherwise non-infectious vector, like capsids, thus, allowing the transport of a further DNA sequence present in said capsid or particle.

Hence, the efficiency of ex vivo or in vivo transduction as well as the applicability of AAV as a delivery tool is increased by increasing the capacity of the transgene to be introduced in the cell accordingly.

That is, in an embodiment, the adeno-associated virus particle according to the present invention carries a functional nucleic acid fragment, or a nucleic acid fragment of a molecule of interest. Said molecule of interest include a nucleic acid fragment encoding a molecule of interest.

The mutated AAV particle according to the present invention with the mutated virus capsid protein or fragment thereof according to the present invention allows to visualize infection of cells by this particle when labeling the same with a labeling group or marker. Thus, a new possibility for studying in vivo the infection as well as the external or internal processing of the virus particle is possible.

In a further aspect, the present invention relates to a nucleic acid molecule encoding the mutated AAV capsid protein or fragment thereof according to the present invention. That is, the nucleic acid molecule according to the present invention is a nucleic acid molecule encoding the AAV capsid protein or fragment thereof of SEQ ID No. 1 or homolog of said sequence whereby, if necessary, a codon optimization may be conducted depending on the host cell.

A further aspect relates to a nucleic acid vector, for example in form of a plasmid, comprising the nucleic acid molecule according to the present invention. The skilled person is well aware of suitable plasmids and vectors. In particular, based on the host cell to be transfected, the plasmid or vector is selected accordingly.

In a further aspect, a host cell containing the nucleic acid vector according to the present invention or the nucleic acid molecule according to the present invention is provided.

The host cell may contain further plasmids, the so-called helper plasmids containing e.g. the rep open reading frame and an adeno viral plasmid with E4, E2A and VA for the production of the recombinant AAV particles.

In a further aspect, a composition is provided comprising an infectious AAV particle containing a mutated AAV capsid protein according to the present invention in combination with at least one non-infectious AAV particle containing a mutated AAV capsid protein whereby the infectious AAV particle is covalently linked to at least one non-infectious particle. Linkage may be as described above, including the click chemistry but also via disulfide bond. In case of the presence of a disulfide bond, said disulfide bond may be dissolved in endosomes at low pH, e.g. below pH 4.5, like below pH 4.0, like below pH 3.5, e.g. pH 3.

In an embodiment of said composition, the non-infectious AAV particle contains a mutated AAV capsid protein having substitutions of at least one of R585A and R588A.

As described above, a composition of an infectious AAV particle according to the present invention with an at least one non-infectious AAV particle or non-infectious non-AAV virus particle enables trans-splicing technology or two component systems to be used for transduction of target cells ex vivo or in vivo. That is, the infectious AAV particle allows to transport the non-infectious particle into the target cell, thus, increasing the capacity of DNA to be introduced into said cell accordingly. Alternatively, both particles are non-infectious and targeting is achieved by a targeting ligand present and bound via the cysteine on at least one of the AAV particles or the targeting is achieved by further genetic introduction of a targeting ligand into the AAV capsid. The composition may be provided in form of a kit. Typically, said kit contains further components for transduction of target cells. Said further components may be buffer or other media for enabling transduction of the target cells. In an embodiment, this kit may also comprise target cells and/or instructions for transduction. In an embodiment of said composition or kit, the composition or kit comprise the AAV particle according to the present invention, or the nucleic acid molecule according to the present invention, or the nucleic acid vector according to the present invention. In another embodiment, the present invention relates to a gene vaccine comprising the AAV particle according to the present invention, or the nucleic acid molecule according to the present invention or the nucleic acid vector according to the present invention or the composition according to the present invention with suitable DNA based vaccine components. Said DNA based vaccine components may be known DNA vaccines or DNA encoding suitable peptides or proteins accordingly. Further, the present invention relates to the use of the AAV particle according to the present invention, the nucleic acid molecules according to the present invention or the nucleic acid vector according to the present invention in the manufacture of a preparation for obtaining AAV binding protein or in the manufacture of a medicament for gene therapy or in the manufacture of a DNA vaccine.

In a further aspect, the present invention relates to a method for the chemical modification of a mutated AAV particle, in particular, a mutated AAV particle according to the present invention. The method comprises a) providing a solid substrate with a binding partner of a binding molecule present on the AAV;

b.) coupling the mutated AAV particle to the solid substrate through binding of the binding molecule with the binding partner, thus, forming a binding pair composed of the binding molecule and the binding partner;

c.) reacting the cysteine present on the surface of the mutated AAV particle bound to the solid substrate with a coupling reagent, in particular for obtaining a thiolether based linker:

d.) washing the column;

e.) optionally coupling an azide containing agent, f.) eluting the modified AAV particle.

The solid substrate may be—as described here—a column containing A20 antibodies coupled to sepharose beads for binding to intact AAV2 capsids. The solid substrate may also be other affinity chromatography materials allowing for specific binding of AAV capsid (natural occurring serotypes or engineered capsids).

Further, the binding partner present on the solid substrate may be an antibody or may be another molecule, like heparin allowing specific binding of the mutated AAV.

The binding molecule present on the mutated AAV particle may be a naturally occurring binding molecule or a molecule specifically introduced into the mutated AAV particle. In an embodiment, the binding molecule may be any one of the VP proteins of the capsid proteins.

In an embodiment, the method for the modification of a mutated AAV particle according to the present invention is a method comprising a) providing an antibody affinity chromatography column containing an antibody binding specifically to AAV particle;

b) coupling of AAV particle according to the present invention to said antibody affinity chromatography column;

c) reacting the cysteine present in AAV particle bound to the column with a coupling reagent, in particular for obtaining a thioether based linker;

d) washing the column;

e) optionally coupling an azide containing agent, f) eluting the modified AAV particle.

The thus modified AAV particles are ready for use or are ready for further modification by CLICK chemistry or other types of covalent linkage including labelling molecules, targeting molecules or a second infectious or non-infectious AAV particle or other virus particles.

That is, not only a purification or enrichment of the AAV particle according to the present invention based on affinity column is described, but also and even more important, chemical modification of said AAV particle on the column is possible while the particle itself remains on the affinity column due to binding to a specific antibody. In particular, the antibody is an antibody allowing to detect only intact capsids but not capsid subunits as described e.g. for the monoclonal antibody A20.

Other methods for particle purification are described in the art including density gradient centrifugation and chromatography including ion exchange, affinity or gel filtration. However, a further modification of a bound particle on the affinity column is not described in the art.

That is, the method according to the present invention comprises providing the cell lysate containing AAV preparation which was pre-purified by known methods, including removing free nucleic acids after nuclease treatment, separating larger impurities as well as larger cell debris.

In addition, an antibody affinity chromatography column is provided. Said column contains antibodies binding specifically to AAV particle while the antibodies are bound to the column material by known methods typically via the Fc moiety.

The pretreated cell lysate is then loaded onto the column, thus enabling coupling of the AAV particle to said antibody affinity chromatography column via binding to the antibodies. After washing of the column containing the AAV particle according to the present invention bound via antibody binding to the column, a further modification is possible. Namely, the cysteine present in the AAV particle bound to the column are reacted with a coupling reagent, typically, a bispecific linker compound, via the thiol group of the cysteine. Typically, a thioether bond is formed, allowing binding of said coupling reagent, e.g. the linker, to the AAV particle accordingly. Next, a washing step is conducted.

Depending on the further compounds or ligands to be bound to the AAV particle via the coupling reagent, further steps are conducted. For example, the linker is further modified by introducing an azide group as part of the click chemistry.

After washing, coupling of a desired ligand is possible including the ligands described above including label or marker or targeting molecules as well as non-infectious AAV particles.

That is, in an embodiment the method according to the present invention comprise binding of a non-infectious AAV particle via the azide group, thus, obtain a composition as defined herein, namely, a composition comprising an infectious AAV particle containing a mutated AAV capsid according to the present invention and a non-infectious AAV particle containing a mutated AAV capsid protein, like having substitutions of at least one of R585A and R588A, whereby the infectious AAV particle is covalently linked to the at least one non-infectious AAV particle.

After modification, the modified mutated AAV particle is eluted from the column.

The elution of the modified AAV particle from the column after on-column modification or after simple purification is conducted e.g. by pH change. For example, a change of the pH value from pH 7 to pH 3 allows to elute the AAV particles without having negative drawbacks on transduction. Further, the change to low pH does not destroy the capsid nor interferes with primary receptor binding.

Thus, the method allows an on-column coupling strategy whereby the coupling of a desired ligand with the AAV particle is conducted while the AAV particle is bound to the column.

It is demonstrated in that the coupling ability and specificity of the artificially introduced cysteine residues into the mutated AAV capsid protein according to the present invention allow the chemical modification.

The modification may also be effected by adding a linking group containing a thiol reactive maleimide group, thus, allowing to covalently bind the group accordingly. For example, biotinylation of the AAV particle is possible allowing for use of binding partners of biotin coupled to label, marker or targeting molecules.

The modified mutant AAV particle allows to direct the infectious particle towards cells that are normally refractive for wild type AAV particles or to desired cell type/s.

Further, in another strategy a composition of infectious and non-infectious AAV particle or infectious AAV particle and non-infectious non-AAV particle may be used for transduction of cells. Thus, the AAV particle described herein represents a new AAV platform for targeted cell entry.

Thus, in a further aspect, a method for co-delivery of infectious AAV particle in at least one non-infectious AAV particle into a target cell comprising the step of contacting the composition as defined herein with a target cell is described.

Thus, a new cell entry targeting platform is provided allowing change of the tropism of the AAV particle on the one hand due to changing the binding capacity to the primary receptor of AAV, namely, the heparan sulfate proteoglycan. It is known that attachment of AAV, like AAV-2 to HSPG is mediated by six residues, namely, R484, R487, K527, K532, R585 and R588. Change of the tropism is e.g. effected by mutating residues R585 and R588. Thus, by mutating at least one of these residues identified above, in particular, any one of the six residues identified above, allows to change the tropism of the AAV particle according to the present invention, in particular, allows to redirect the cell targeting accordingly if e.g. combined with target ligand inclusion.

To conclude, it is possible to use the ligand covalently linked to the newly introduced cysteine present in the mutated AAV capsid protein by covalent binding as a cell entry possibility or cell entry platform for single vectors but also complexes of two or more vectors as described herein.

Of course, it is also possible not to use an AAV non-infectious particle but to use an non-infectious particle derived from other virus or from a nanoparticle which should be co-delivered into the target cell accordingly. The targeting to the target cell is effected by the AAV particle according to the present invention, e.g. by linkage of a suitable ligand via the cysteine.

Hence, a further aspect relates to the use of the composition according to the present invention in ex vivo and in vivo gene therapy methods. In addition, the present invention relates to methods including the administration of the mutated AAV particle according to the present invention or the nucleic acid molecule or nucleic acid vector according to the present invention.

The skilled person is well aware of the administration steps required for administering the particles ex vivo or in vivo.

Thus, in an aspect the present invention relates to a method for reducing one or more symptoms of a disease in a subject comprising administering to said subject a therapeutic amount of the mutated capsid protein or the mutated AAV particle as well as the nucleic acid molecule or nucleic acid vector as described herein or a composition or a gene vaccine described herein.

The AAV particle, e.g. the non-infectious AAV particle or, the non-infectious AAV particle containing a covalently linked targeting molecule as described herein or the tropism-modified infectious AAV generated by a genetic targeting approach as described herein may contain a molecule of interest as described herein, e.g. a molecule of interest useful in the treatment of cancer covalently attached to the capsid via the introduced cysteine residues.

Thus, a pharmaceutical composition is disclosed, comprising at least one of the mutated AAV capsid protein or fragment thereof according to the present invention, a mutated AAV particle according to the present invention, a nucleic acid molecule according to the present invention and/or a nucleic acid vector according to the present invention, and, in particular, a composition or kit according to the present invention as well as a gene vaccine according to the present invention. Said pharmaceutical composition or medicament may contain other suitable components including diluents, excipients or carriers.

The medicament may be useful for the treatment or prevention of cancer or tumors as well as infectious diseases, neurodegenerative diseases or allergic diseases. That is, the present invention relates to a method of treating and/or preventing a disease, the method comprising the step of administering to a subject in a need thereof a pharmaceutically or therapeutically effective amount of the pharmaceutical composition or medicament as described herein, wherein the disease is selected from the consisting of an allergic disease or asthma, Alzheimer disease, arteriosclerosis or other degenerative diseases, a tumor disease, an autoimmune disease or a chronic informatory disease as well as infectious disease.

Further, the particles and compositions described herein are suitable for the use as a vaccine, preferably, for preventing or treating an autoimmune disease and/or chronic informatory disease, a tumor disease, an allergic disease, asthma, Alzheimer disease, arteriosclerosis, a metabolic disease, an informatory disease, a neurological disease or to be used in ophthalmology.

Further, a method for co-delivery of infectious or non-infectious AAV particle and at least one non-infectious AAV particle into a target cell comprising the step of contacting a composition according to the present invention with target cells is provided.

The invention will be described further by way of examples without limiting the same thereto.

Examples

Affinity Chromatography for On-Column Coupling of Cys-Containing AAV Vectors
Preparation of A20 Affinity Column HiTrap™ NHS-activated High Performance (GE Healthcare) was washed with 10 ml ice-cold 1 mM HCl to remove contaminating isopropanol. Then monoclonal AAV2-specific A20-antibody was diluted with coupling buffer [0.2M NaHCO$_3$, 0.5 M NaCl, pH 8] to a final volume of 2 ml at a concentration of 250 µg/ml and loaded on the column using a P1-Pump, to let primary amines of the antibody react with NHS groups of the column for three hours in an infinite loop. For determination of coupling efficiency, 3 ml of coupling buffer was injected and later analyzed. Deactivation of any excess of active groups that were not coupled to the ligand was performed by using alternatively buffer A [0.5 M ethanolamine, 0.5 M NaCl, pH 8.3] and buffer B [0.1 M sodium acetate, 0.5 M NaCl, pH 4] according manufacturers instruction. For storage column was sealed and stored in storage buffer [0.05 M Na$_2$HPO$_4$, 0.1% NaN$_3$, pH 7] at 4° C. until next use. One column was used up to 10 times.
Affinity Chromatography to Purify or Concentrate AAV Vectors from Cell Lysate Or after Density Gradient Purification in Preparation of Coupling Reaction To purify from lysates of vector producing cell and/or concentrate AAV vectors for example following density gradient purification, samples were loaded on an affinity column. Columns were connected to a peristaltic pump (Pump P-1; Amersham Biosciences), which was run with a maximum flow rate of 300 µl/ml. Columns were first equilibrated using 10 ml of 20 mM HEPES, pH 7. Then, benzonase treated and centrifuged cell lysate of vector producing cells were loaded onto the respective column. Flow-through was collected to determine the amount of bound particles. After this, any unbound vector was washed out with 10 ml of 20 mM HEPES, pH 7 and eluted. In case of an A20-affinity chromatography, bound vectors were eluted with 0.2 M Glycine, pH 3, while in case of heparin affinity chromatography, bound vectors were eluted by high salt buffer (e.g. 20 mM HEPES/1M NaCl.)
Examples of Coupling Reactions:
With Maleimide-PEG$_2$-Biotin or Maleimide-PEG$_4$-DBCO Vector preparations were incubated with 25 mM Tris(2-carboxyethyl)phosphine hydrochloride (TCEP) for 1 hour at room temperature to ensure cysteine reduction. Vector solution was then loaded onto a HiTrap™ Heparin HP column. A washing step with 20 mM HEPES pH 7.3 was performed before Maleimide-PEG-biotin in a 50 molar excess over cysteines was loaded onto the column and incubated for 3 hours in an infinite loop. A final washing step with 20 mM HEPES, pH 7.3 was added before coupled vectors were eluted using 20 mM HEPES/1M NaCl.

With Azide-Modified Molecules

Genomic titer was determined and purified vector solution was loaded onto a HiTrap™ Heparin HP column or A20 column (for Cys2$^{\Delta HSPG}$) following TECP treatment. A washing step with 20 mM HEPES, pH 7.3 was performed before a Dibenzylcyclooctyne-PEG$_4$-Maleimid linker in a 100 molar excess over cysteines was loaded onto the column and incubated for 3 hours in an infinite loop. After another washing step, azide-modified molecules (e.g. azide modified targeting ligands) were added and incubated for 72 hours in an infinite loop. A final wash step with 20 mM HEPES, PH 7.3 was added before coupled vectors were eluted using with 1 M HEPES, pH 7.2 or 0.2 M Glycine, pH 3 for Cys2$^{\Delta HSPG}$ respectively.

Coupling of Two AAV Vectors

The coupling reaction takes place on a heparin column. The purified vectors are treated with TCEP for an hour at room temperature in a 1:10 ratio afterwards the vectors are diluted 1:20 with 20 mM HEPES. The heparin column is washed with 20 ml 20 mM HEPES and the AAV preparation containing the infectious vector particles is loaded onto the column with a flow rate of 1 ml per minute. The flow through is pumped over the column a second time and the column is washed with 25 ml 20 mM HEPES. The Azido-Maleimide-Linker working solution is prepared as described in the producer's manual and diluted in 5 ml 20 mM HEPES. The diluted linker solution is pumped over the column at slowed flow rate for three hours. Afterwards the column is washed with 30 ml 20 mM HEPES to wash out unbound linker. The DBCO linker is put onto the column over night at a slow flow rate in a 100 time access to the cysteine residues in the vector capsids. The following morning the column is washed with 35 ml 20 mM HEPES. The second vector (non-infectious=non-HSPG (heparin) binding vector) is treated with TCEP as well and then put onto the column at a flow rate of 1 ml per minute. The flow through is pumped over the column a second time and the column is washed with 30 ml 20 mM HEPES. Coupled vectors are eluted with 20 mM HEPES supplemented with 1.5M NaCl$_2$. Ten fractions with an approximate volume of 500 μl are eluted. The fractions are analyzed with qPCR to determine the genomic titer using transgene specific primers. Furthermore, presence of vector genomes from infectious AAV (binds to the column) and non-infectious AAV (possess a compromised HSPG binding ability) in the same fraction indicates a successful coupling reaction.

Analyses of Modified Vectors

Cell Transduction Assays

Cells were seeded in a 48 well plate at a density of 2×10$^4$ cells/well and 24 hours later cells of one well were counted to calculate respective GOI (Genome of infection= Transgene containing particle/cell). Cells were incubated with vector preparation at desired particle-per-cell ratio. 24 hours or 48 hours post transduction, cells were harvested, washed and resuspended in PBS and analyzed via flow cytometry.

| Material | |
| --- | --- |
| HiTrap ™ NHS-activated HP column (1 ml) | Amersham/GE Healthcare, Freiburg, Germany |
| TCEP | Invitrogen, Karlsruhe, Germany |
| HEPES (liquid) | PAA laboratories, Pasching, Austria |
| Ethanolamine | Fluka, Sigma-Aldrich, Taufkirchen, Germany |
| DBCO-PEG$_4$-Maleimide | Jena Bioscience, Jena, Germany |

-continued

| Antibody: | | | | |
| --- | --- | --- | --- | --- |
| Specification | Host | Application | Dilution | Company |
| Anti-AAV2 intact capsid (A20) | mouse | ELISA, IF, AC | pending | Progen, Heidelberg, Germany |

Plasmids peGFP (Self-Complementary):

AAV vector plasmid that encodes for *Aequorea Victoria* enhanced Green Fluorescent Protein (eGFP) gene under the control of the human Cytomegalovirus (CMV) promoter. The transgene cassette is flanked by the AAV2 ITRs. A deletion in one of the TRS interferes with strand displacement resulting in a self-complementary genome conformation, which is packaged into the viral capsid; Ampicillin-resistance peCrimson (Self-Complementary):

AAV vector plasmid that encodes for Crimson gene under the control of the human Cytomegalovirus (CMV) promoter. The transgene cassette is flanked by the AAV2 ITRs. A deletion in one of the TRS interferes with strand displacement resulting in a self-complementary genome conformation, which is packaged into the viral capsid; Ampicillin-resistance pxX6-80:

Adenoviral helper plasmid encoding for VA, E2A and E4; Ampicillin resistance. Required for packaging.

Cys2:

AAV helper plasmid, encoding for the Rep and Cap proteins of AAV2 with 5 mutations within the cap sequence leading to substitutions at the amino acid position 449 (N→I), 458 (S→C), 459 (R→M), 493 (A→D) and 551 (N→C). Ampicillin resistance Cys2$^{\Delta HSPG}$:

AAV helper plasmid, based on the plasmid Cys2. Two additional mutations at amino acid position 585 (R→A) and 588 (R→A) are introduced via site-directed mutagenesis to ablate wt tropism (=compromised HSPG binding ability), Ampicillin resistance Eukaryotic Cells

CHO-K1

Chinese hamster ovary cell line; American Type Culture Collection (ATCC) number: CCL-61

CHO-K6

Chinese hamster ovary cell line genetically engineered to express HER2/neu receptor, kindly provided by Christian Buchholz, Paul-Ehrlich-Institute, Langen

HEK-293

Human embryonic kidney cells, transformed with Ad5 DNA containing the adenoviral genes E1a and E1b; ATCC number: CRL-1573

MCF-7

Human breast cancer cell line, ATCC number: HTB-22

Figure 2:
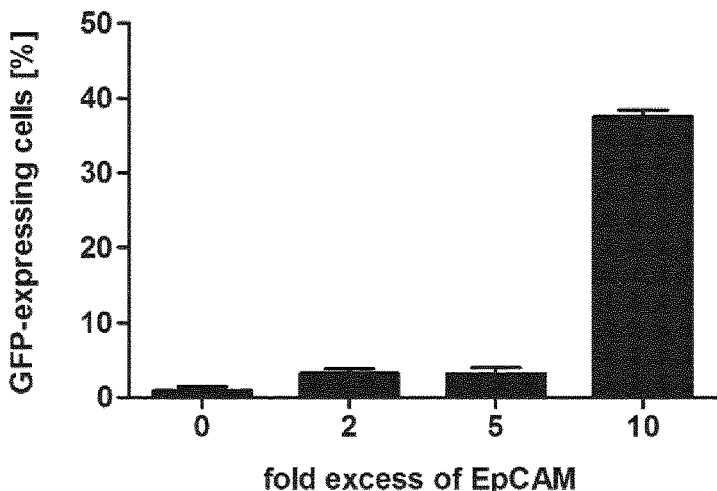
FIG. 2: MCF-7 cells were incubated with $5\times10^4$ of $Cys2^{\Delta HSPG}$ (neg. control) or the EpCAM-$Cys2^{\Delta HSPG}$ vector. The latter was produced by incubating DARPins in excess at the indicated ratios. GFP-expression was measured by flow cytometry 48 hours p.t. Values represent the mean of three independent experiments, error bars represent ±SD.
Figure 3:
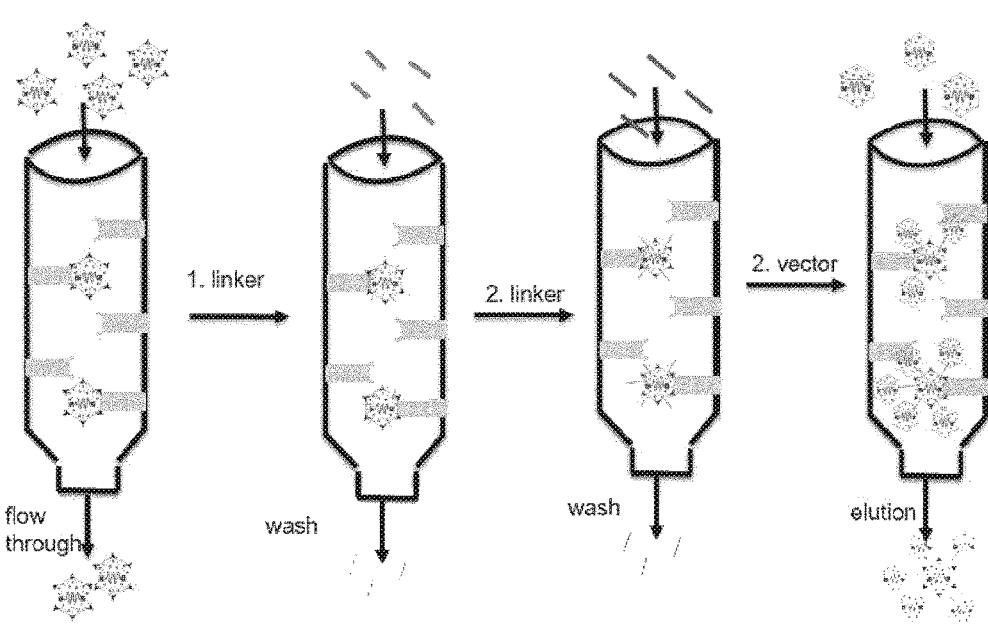
FIG. 3: First, infectious (eGFP encoding) AAV vector is bound to the heparin column. Then linkers are added as described, followed by addition of non-infectious (Crimson encoding) vector. After a washing step, particles are eluted in 10 fractions and subjected to qPCR analyses.
Figure 4:
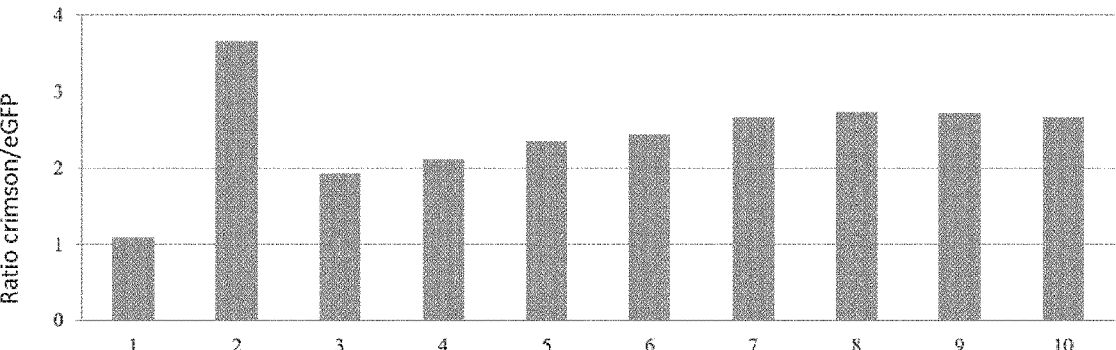
FIG. 4: The bound particles were eluted in fractions. Aliquots of each fractions were analyzed. Specifically, total DNA was isolated using the Dneasy Blood and Tissue kit (Qiagen). DNA was subjected to qPCR using primers for eGFP (encoded in vector genome of infectious AAV particle) and for Crimson (encoded in vector genome of non-infectious AAV particle). Shown is the ratio of crimson vector genomes to eGFP vector genomes. Since the non-infectious particle shows depletion of main residues of the HSPG binding motifs it is compromised in its column binding ability, presence of Crimson encoding vector genomes in elution hints towards a successful coupling.
Figure 5:
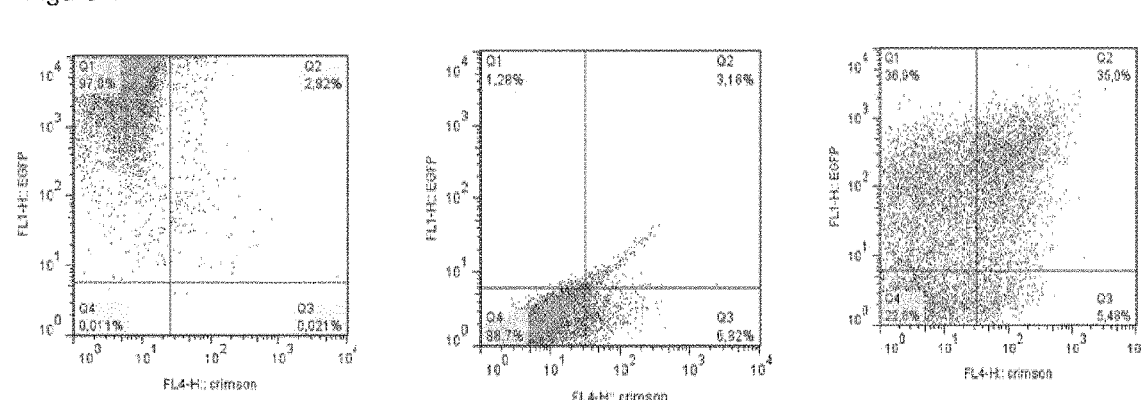
FIG. 5: Hela cells were incubated with the infectious AAV vector encoding for eGFP (left) or with non-infectious AAV vector encoding for Crimson (middle). Number of trans-duced cells were determined by flow cytometry. These results reveal that infectious AAV particle preparation con-tains infectious particles, while with non-infectious AAV particle preparations transduced cells remained at back-ground level. Incubation of Hela cells with the same par-ticle-per-cell ratio with fraction 2 of "A" (see FIG. 4) resulted in eGFP/Crimson double-positive cells indicating a successful co-infection.

As shown in the figures, successful receptor targeting with the proteins and particles of the present invention is possible, see FIGS. 1 and 2. In addition, the modification and, thus, the preparation of a composition of a dual vector system is possible, see FIGS. 3 to 5.

The invention claimed is:

1. A mutated adeno-associated virus (AAV) capsid protein or a fragment thereof, wherein an amino acid of the wild type adeno-associated virus capsid protein of SEQ ID NO: 1 or a fragment thereof or a homolog of SEQ ID NO: 1 have a substitution of a wild type non-cysteine amino acid into a cysteine whereby the wild type non-cysteine amino acid is present on an outer surface of the capsid when the capsid is assembled as an AAV particle, wherein the substitution of the non-cysteine amino acid into cysteine is at at least two positions selected from position 458, 459, 551, 446, or 525 of SEQ ID NO:1 or the homolog thereof.

2. The mutated AAV capsid protein or a fragment thereof according to claim 1 wherein the at least two positions are position 458, and position 551 of SEQ ID NO: 1 or the homolog thereof.

3. The mutated AAV capsid protein or a fragment thereof according to claim 1, further comprising either a substitution of R459M or a substitution of R459C.

4. The mutated AAV capsid protein or a fragment thereof according to claim 1, wherein the AAV is type 2 AAV.

5. The mutated AAV capsid protein or a fragment thereof according to claim 1, further comprising a labeling group, targeting molecule, or ligand linked to the cysteine.

6. The mutated AAV capsid protein or a fragment thereof according to claim 5 wherein the labeling group is at least one of a fluorescence labeling group or a labeling group capable of occurring a click chemistry with an azide, wherein the targeting molecule is linked to a group capable of occurring a click chemistry with azide, or wherein the ligand is linked to the cysteine via a maleimide binding whereby the linkage is via thioether group.

7. A mutated adeno-associated virus (AAV) particle comprising the mutated adeno-associated particle virus capsid protein or a fragment thereof according to claim 1.

8. The mutated adeno-associated virus particle according to claim 7, further comprising a linker allowing coupling of at least a second, different mutant adeno-associated virus particle.

9. A nucleic acid molecule encoding the mutated adeno-associated virus capsid protein or fragment thereof according to claim 1.

10. A nucleic acid vector, comprising the nucleic acid molecule according to claim 9.

11. An isolated host cell containing the nucleic acid molecule according to claim 10.

12. A composition or kit comprising an infectious AAV particle containing a mutated AAV capsid protein according to claim 1 and a non-infectious AAV particle, whereby the infectious AAV particle is covalently linked to at least one non-infectious AAV particle.

13. The composition or kit comprising an infectious AAV particle according to claim 12 wherein the mutation rendering the particle non-infectious is at least one substitution at position R585A or R588A.

14. A composition or kit, which comprises the AAV particle according to claim 7.

15. A method for producing a mutated adeno-associated virus (AAV) particle comprising a mutated adeno-associated virus (AAV) capsid protein or a fragment thereof, wherein an amino acid of the wild type adeno-associated virus capsid protein of SEQ ID NO: 1 or a fragment thereof or a homolog of SEQ ID NO: 1 have a substitution of a wild type non-cysteine amino acid into a cysteine whereby the wild type non-cysteine amino acid is present on an outer surface of the capsid when the capsid is assembled as an AAV particle, wherein the substitution of the non-cysteine amino acid into cysteine is at at least two positions selected from position 458, 459, 551, 446, or 525 of SEQ ID NO: 1 or the homolog thereof comprising:

a) providing a solid substrate with a binding partner of a binding molecule present on the AAV;

b) coupling the mutated AAV particle to the solid substrate through binding of the binding molecule with the binding partner, thus, forming a binding pair composed of the binding molecule and the binding partner;

c) reacting a cysteine present on a surface of the mutated AAV particle bound to the solid substrate with a coupling reagent;

d) washing the solid substrate;

e) optionally coupling an azide containing agent, f) eluting a modified AAV particle.

16. A method for producing a mutated adeno-associated virus (AAV) particle comprising a mutated adeno-associated virus (AAV) capsid protein or a fragment thereof, wherein an amino acid of the wild type adeno-associated virus capsid protein of SEQ ID NO: 1 or a fragment thereof or a homolog of SEQ ID NO: 1 have a substitution of a wild type non-cysteine amino acid into a cysteine whereby the wild type non-cysteine amino acid is present on an outer surface of the capsid when the capsid is assembled as an AAV particle, wherein the substitution of the non-cysteine amino acid into cysteine is at at least two positions selected from position 458, 459, 551, 446, or 525 of SEQ ID NO: 1 or the homolog thereof comprising:

a) providing an antibody affinity chromatography column containing an antibody binding specifically to the AAV particle;

b) coupling of the AAV particle to said antibody affinity chromatography column;

c) reacting a cysteine present in the AAV particle bound to the column with a coupling reagent;

d) washing the column;

e) optionally coupling an azide containing agent, f) eluting the modified AAV particle.

17. The method according to claim 16 further comprising e) coupling an azide containing agent and further comprising binding of a non-infectious AAV particle via the azide group.

18. The method according to claim 15 further comprising e) coupling an azide containing agent, and further comprising binding of a non-infectious AAV particle via the azide group.

19. The method according to claim 15 wherein step c) obtains a thiolether based linker.

20. The method according to claim 16 wherein step c) obtains a thiolether based linker.

21. A composition or kit comprising an infectious AAV particle and a non-infectious AAV particle, wherein the infectious AAV particle and the non-infectious AAV particle contain the mutated AAV capsid protein or fragment thereof according to claim 1 with the proviso that the non-infectious AAV particle has substitutions of at least one of R585A and R588A, whereby the infectious AAV particle is covalently linked to at least one non-infectious AAV particle.

22. The composition or kit according to claim 21 wherein the infectious AAV particle is covalently linked to the non-infectious AAV particle by a process of click chemistry.

23. The method according to claim 15 wherein the process further comprises binding of a non-infectious AAV particle via the azide group.

24. The method according to claim 16 wherein the process further comprises binding of a non-infectious AAV particle via the azide group.

25. The mutated adeno-associated virus-particle according to claim 7 further comprising a labeling group, a targeting molecule or ligand linked to the cysteine.

\* \* \* \* \*